(12) United States Patent
Allen et al.

(10) Patent No.: US 6,996,436 B2
(45) Date of Patent: Feb. 7, 2006

(54) DEFIBRILLATOR WITH UNCONTROLLED SOLID STATE SWITCHING

(75) Inventors: James Allen, Ballyclare (GB); John McCune Anderson, Holywood (GB); Allister Robert McIntyre, Newtownards (GB)

(73) Assignee: Heartsine Technologies, Inc., County Antrim (GB)

( * ) Notice: Subject to any disclaimer, the term of this patent is extended or adjusted under 35 U.S.C. 154(b) by 575 days.

(21) Appl. No.: 10/182,746

(22) PCT Filed: Feb. 13, 2001

(86) PCT No.: PCT/IB01/00439

§ 371 (c)(1),
(2), (4) Date: Jul. 30, 2002

(87) PCT Pub. No.: WO01/60454

PCT Pub. Date: Aug. 23, 2001

(65) Prior Publication Data

US 2003/0023276 A1    Jan. 30, 2003

(30) Foreign Application Priority Data

Feb. 18, 2000    (IE) .............................. S2000/0140

(51) Int. Cl.
*A61N 1/39*    (2006.01)

(52) U.S. Cl. .............................................. 607/5; 607/4
(58) Field of Classification Search .................... 607/4, 607/5, 15
See application file for complete search history.

(56) References Cited

U.S. PATENT DOCUMENTS

| 4,998,975 | A | * | 3/1991 | Cohen et al. ................... 607/5 |
| 5,178,140 | A | * | 1/1993 | Ibrahim ......................... 607/5 |
| 5,776,165 | A | * | 7/1998 | Ripart ........................... 607/5 |
| 6,317,628 | B1 | * | 11/2001 | Linder et al. ............... 600/547 |
| 6,353,758 | B1 | * | 3/2002 | Gliner et al. .................. 607/5 |

* cited by examiner

*Primary Examiner*—Kennedy Schaetzle
*Assistant Examiner*—John D. Alexander
(74) *Attorney, Agent, or Firm*—Porter, Wright, Morris & Arthur, LLP

(57) ABSTRACT

A defribrillator comprises first and second electrodes (A, B) for application to a patient, a voltage source (60), and an output circuit for connecting the voltage source across the electrodes upon the occurrence of a control signal (64). The output circuit includes a first current path connecting one side of the voltage source to the first electrode (A) and a second current path connecting the other side of the voltage source to the second electrode (B). Each of the current paths contains at least one solid state switching device USD1 (bo) or IGBT1. The switching device(s) USD1 (bo) in at least one of the current paths has no external control and characteristics similar to a Shockley diode.

6 Claims, 15 Drawing Sheets

DEFIBRILLATOR WITH UNCONTROLLED SOLID STATE SWITCHING

This invention relates to a defibrillator, in particular but not exclusively an external defibrillator.

External defibrillators correct an abnormal heart rhythm, such as Ventricular Fibrillation (VF) or Ventricular Tachycardia (VT), using a high energy shock pulse delivered to a patient using electrodes attached to the patient's torso. Attaching the electrodes externally to the patient's torso means that these devices can be portable and carried by emergency personnel. Unfortunately, delivering the pulses to the patient's chest externally means that higher energies are required than would be the case for implantable defibrillators that connect directly to the heart's surface. The requirement for higher energies has meant that these devices are larger and heavier than the operators would desire. Reducing both the size and cost of external defibrillators will mean that the devices can be carried with greater ease and that more personnel will be able to afford the devices.

Prior art defibrillators which deliver a monophasic or biphasic truncated exponential waveform do so by applying control or drive signals to an arrangement of silicon devices. Rather than using mechanical switches or relays which provide a direct electrical connection, silicon devices can be driven from a high impedance state to a state of lower impedance using a control signal. This process is much faster than would be obtainable from mechanical switches and allows waveforms of several milliseconds to be accurately produced. These methods, however, are complex and costly due to the need for isolation of the high voltage devices from the low voltage controllers by, for example, the use of opto-isolators or coupling transformers.

Typically, prior art methods have used silicon controlled rectifiers (SCRs) and insulated gate bipolar transistors (IGBTs). These devices can conduct pulses in excess of 1000V using gate drive circuits that are only rated at several tens of volts. However, current commercial devices are incapable of withstanding any more than approximately 1200 Volts. Therefore, in order to conduct pulses in excess of the several thousand volts typically needed for external defibrillation, several devices need to be placed on top of one another. This is a concept known as "totem-poling" and is well known to those skilled in the art. Without totem-poling, the SCRs would spontaneously change to their low impedance state once their maximum voltage rating had been exceeded. Similarly, an IGBT will destructively fail if it's maximum voltage is exceeded. Furthermore, an SCR will spontaneously change state if the rate of change of voltage ($\delta V/\delta t$) is exceeded.

FIG. 1 is shown by way of example and includes two SCRs, SCR1 and SCR2, totem-poled together. In FIG. 1 the gate drive circuit GD2 to the upper device SCR2 is floating above signal ground at point B, which is at a voltage V1 equal to the voltage across the lower device SCR1 between points B and C. It is for this reason that the gate drive to SCR2 needs to be isolated from the common ground point C. In FIG. 1 this isolation is achieved by a transformer coupler T. The transformer allows the pulse to cross the isolation barrier IB without any direct electrical connection. The whole arrangement functions equivalent to a single SCR with increased voltage capability, provided the gate drive waveforms to SCR1 and SCR2 are synchronised. The gate drive waveforms are usually generated by logic circuitry from a timing controller. The use of isolated drive circuits to control these silicon devices means that attempting to reduce the size of the circuit as a whole has limits since large physical gaps or air spaces are required at different areas of the final circuit. Furthermore, the isolators require additional support circuitry and sychronised drive waveforms, all of which occupy physical space in the final design and additional cost.

It is an object of the invention to provide an improved defibrillator in which these disadvantages are mitigated or avoided.

According to an aspect of the invention, there is provided a defibrillator as specified in claim 1 and/or any one or more of the claims dependent thereon.

The invention is also directed to a method by which the described apparatus operates and including method steps for carrying out every function of the apparatus.

In the present specification an "uncontrolled solid state device" (USD) means a two-terminal solid state device which, without the application of any external control signal, automatically undergoes a transition from a high impedance state to a lower impedance state when a voltage greater than a predetermined threshold is applied across its terminals. A USD can be a single integrated component or can be a circuit constructed from multiple solid state components. A basic example of a USD is a Shockley diode.

A "breakover USD" is a USD which transitions to the lower impedance state unconditionally when the applied voltage exceeds the threshold.

A "breakunder" USD is a USD which only transitions to the lower impedance state if the applied voltage does not exceed a second threshold greater than the first threshold.

Embodiments of the invention will now be described, by way of example, with reference to the accompanying drawings, in which:

FIG. 1, previously described, is a circuit illustrating the "totem-poling" of two SCRs so that the combination of the two devices can withstand a higher voltage than a single device;

FIG. 12b is an example of the waveform that can be produced by the embodiment of FIG. 12a.

Figure 1:
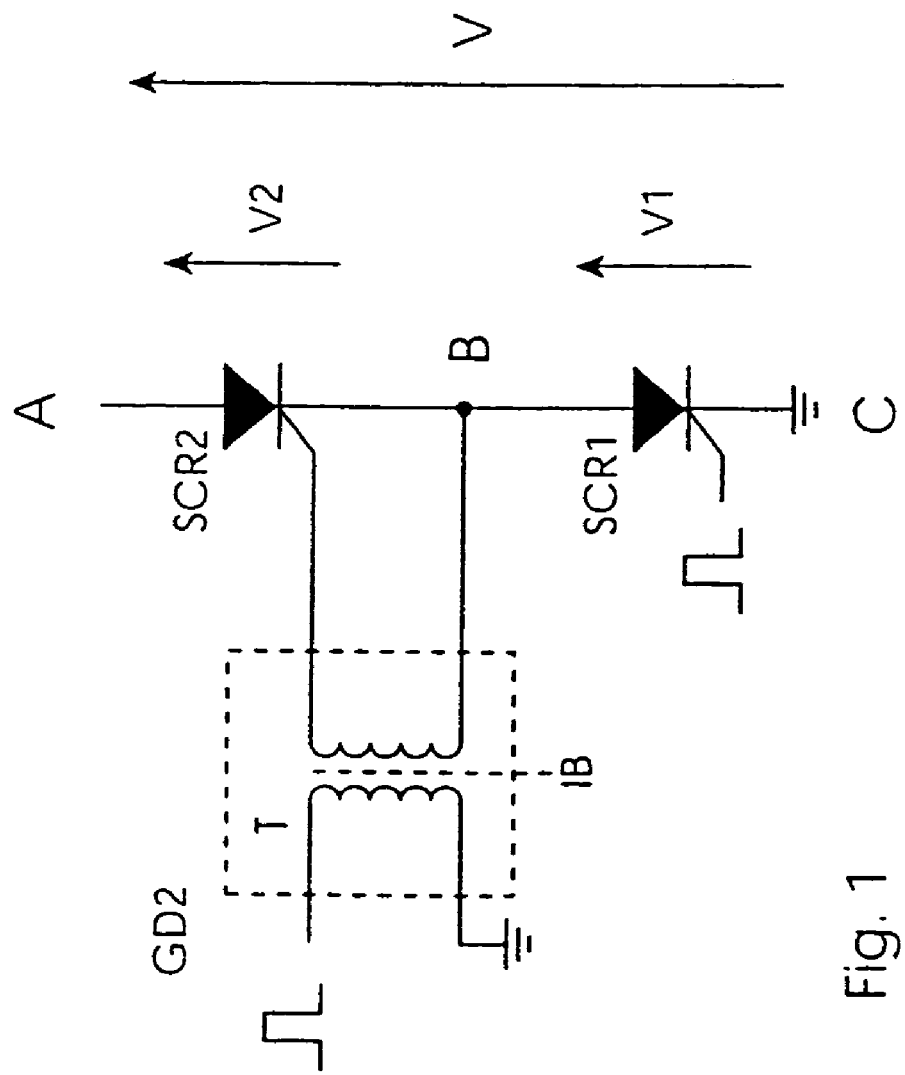
Figure 2:
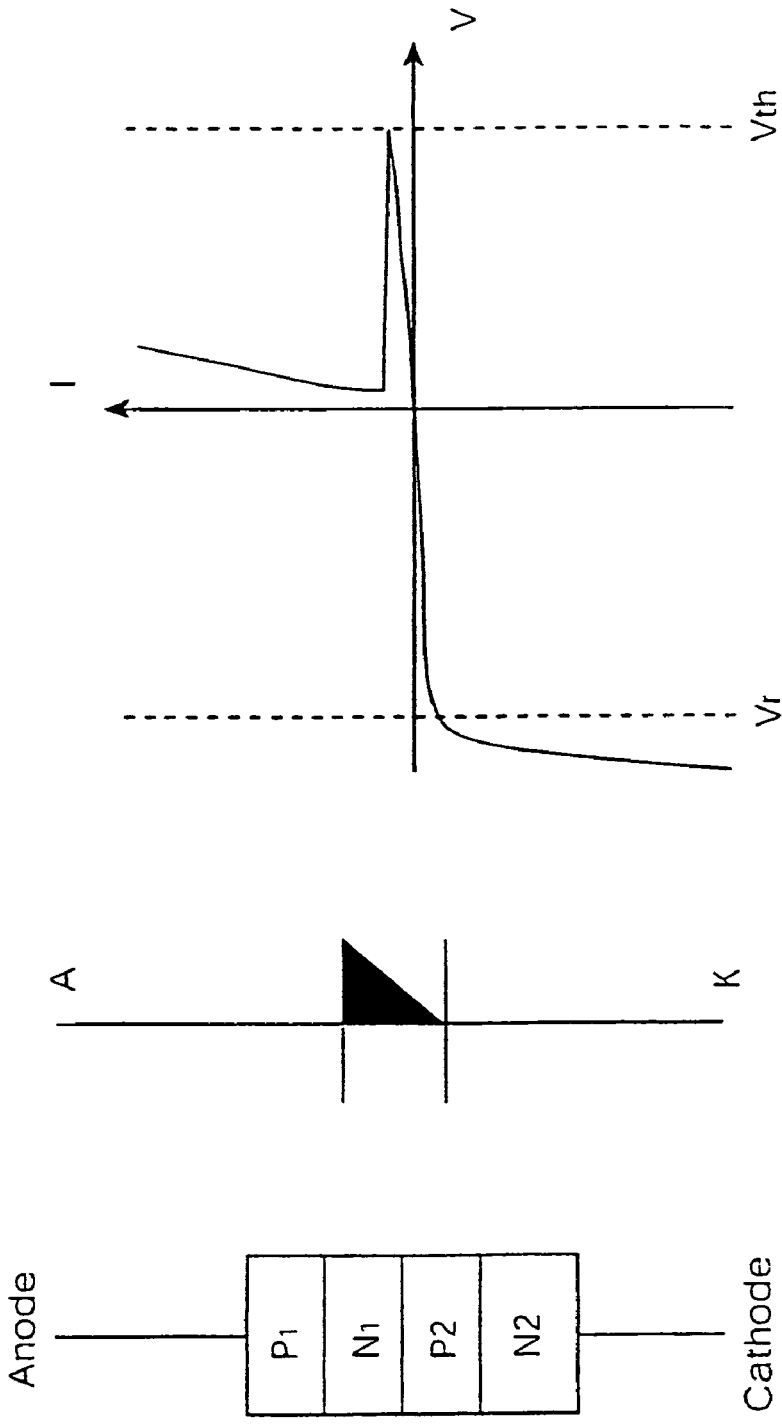
FIGS. 2a, 2b and 2c are, respectively, the substrate construction, circuit symbol and I=V characteristics of a Shockley diode.

The embodiments of the invention to be described herein use devices or circuits having the characteristics of Shockley diodes, and which are referred to herein as uncontrolled solid state devices (USDs) as defined above. Unlike SCRs and IGBTs, a Shockley Diode does not require a gate drive signal to initiate it from a high impedance state to a state of lower impedance. FIG. 2a shows the substrate construction of a Shockley diode as a four layer silicon device with respective doping densities P1, N1, P2 and N2.

FIG. 2b shows the symbol used to denote a Shockley diode; note that there are only two connecting terminals. Essentially a Shockley diode is uni-directional in that it can only change from its default high impedance state to a state of reduced impedance when the polarity of the applied signal is in a particular direction to forward bias the device, see FIG. 2c. Applying a signal of opposite polarity will fail to change the device's state unless the voltage exceeds its reverse breakdown voltage (Vr). A characteristic of a Shockley diode is that as a voltage is applied across the device in the forward bias direction, the device will only change to its lower impedance state if the voltage exceeds a predetermined threshold (Vth). Shockley diodes, however, are not readily commercially available and those that are typically only capable of withstanding small voltages and currents. However, this limitation can be overcome by arranging other commercially available devices to perform the equivalent function for high voltages and currents.

Figure 3:
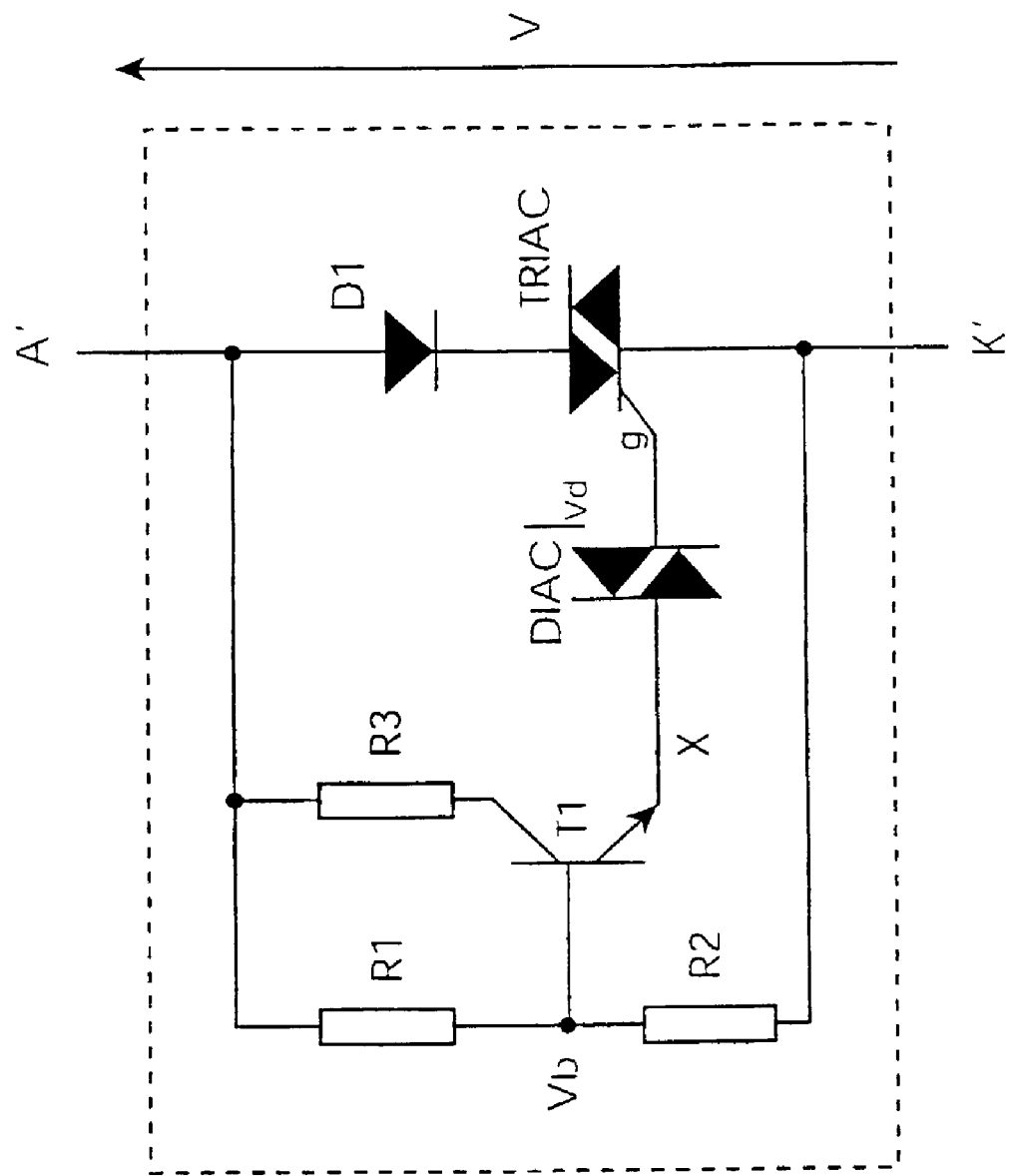
FIG. 3 is a circuit diagram of a breakover USD.

FIG. 3 is a high voltage, high current, implementation of a "breakover" USD, equivalent to a Shockley diode, using a DIAC and a TRIAC. Note that the overall circuit of FIG. 3 has only two terminals, an anode A' and a cathode K'. The TRIAC will change to a state of low impedance allowing a high current to flow when an appropriate voltage is applied to its gate terminal g. The combination of resistors R1 and R2 form a voltage divider, dividing the voltage V down to a voltage Vb, referenced to the cathode K', at the base of the transistor T1, where Vb=V[R2/(R1+R2)]. The emitter follower configuration of transistor T1 keeps the voltage applied to the DIAC at point X at approximately 0.7 Volts below the voltage Vb.

The DIAC will remain in its default high impedance state unless the voltage across it exceeds its threshold voltage Vd. Unless this voltage threshold is exceeded therefore, the USD will remain high impedance between A' and K'. If, however, the voltage at X exceeds the DIAC's threshold Vd, the DIAC will fold back and allow a voltage to appear at the gate of the TRIAC, and the TRIAC will then change to its low impedance state allowing a high current to flow between A' and K'. The overall voltage at which the USD changes state can therefore be accurately set by the voltage divider R1/R2. If the USD is desired to change to its low impedance state when the voltage V across it, i.e. across the terminals A' and K', reaches a certain threshold Vth, then the values of R1 and R2 are chosen such that this voltage Vth causes the voltage at X to be equal to the DIAC threshold voltage Vd; i.e. one solves the equation Vd=[Vth(R2/(R1+R2))]−0.7 for R1 and R2. Resistor R3 limits the current flow into the gate terminal of the TRIAC and prevents the gate from being damaged by the relatively high voltage across the terminals A' and K'. Note that with the state change of the device being determined by the ratio of R1 and R2, and the supply to the DIAC being performed by R3 through the current gain of T1, the values of both R1 and R2 can be kept high. Using high impedance values for R1 and R2 means that in the high impedance state there is very little current leakage through the USD. The diode D1 opposes any current flow in the reverse bias direction and in effect determines the reverse breakdown characteristics for the USD.

Note that any device which can be placed in a low impedance state from an initial state of high impedance could be used in place of the TRIAC in FIG. 3, for example the USD could have employed a combination of IGBTs, SCRs, FETs (field effect transistors) or BJTs (bipolar junction transistor). The various implementations possible will be known to those skilled in the art.

Figure 4A:
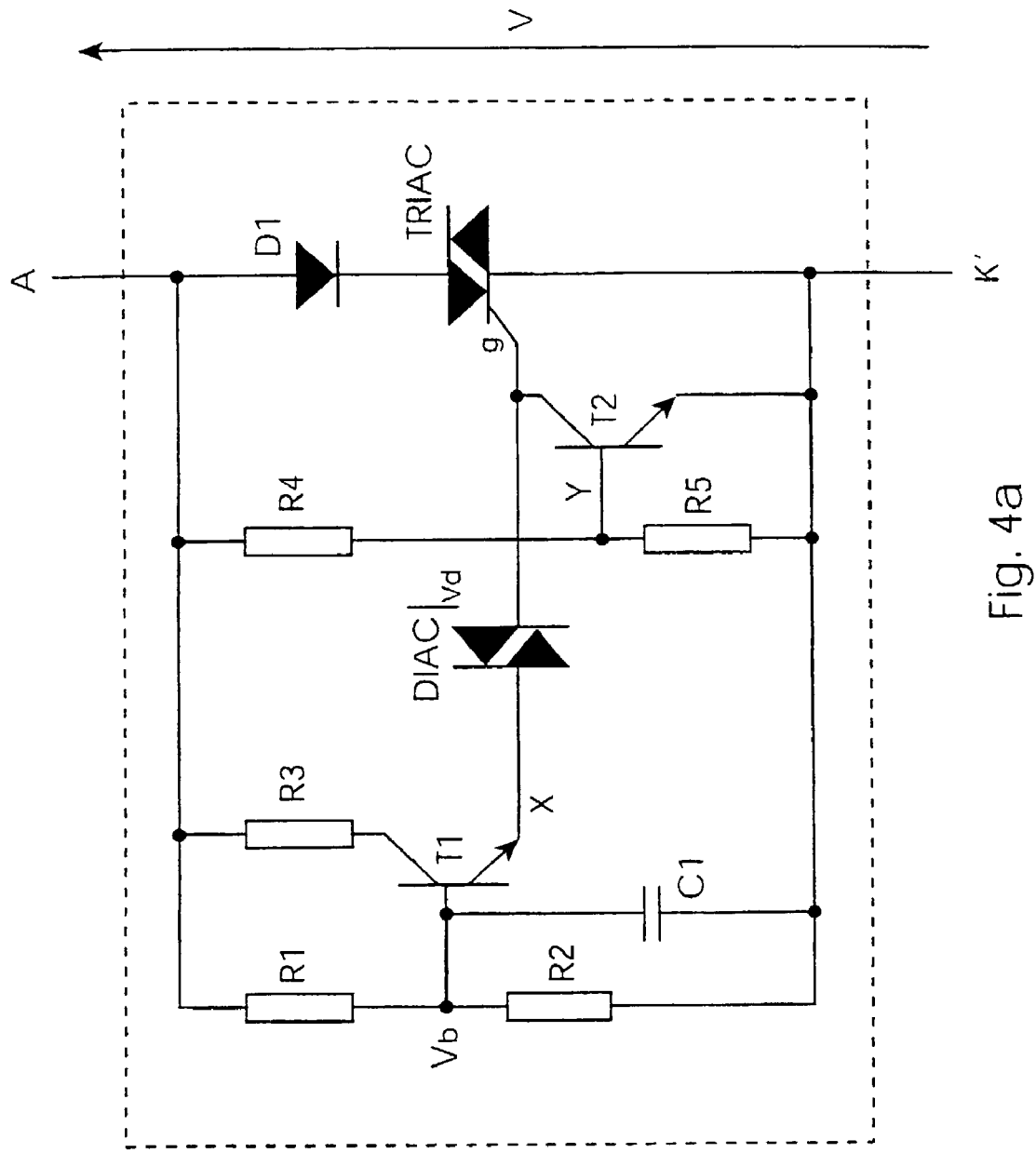
FIGS. 4a, 4b and 4c are, respectively, a circuit diagram, circuit symbol and I=V characteristics of a breakunder USD.
Figure 4C:
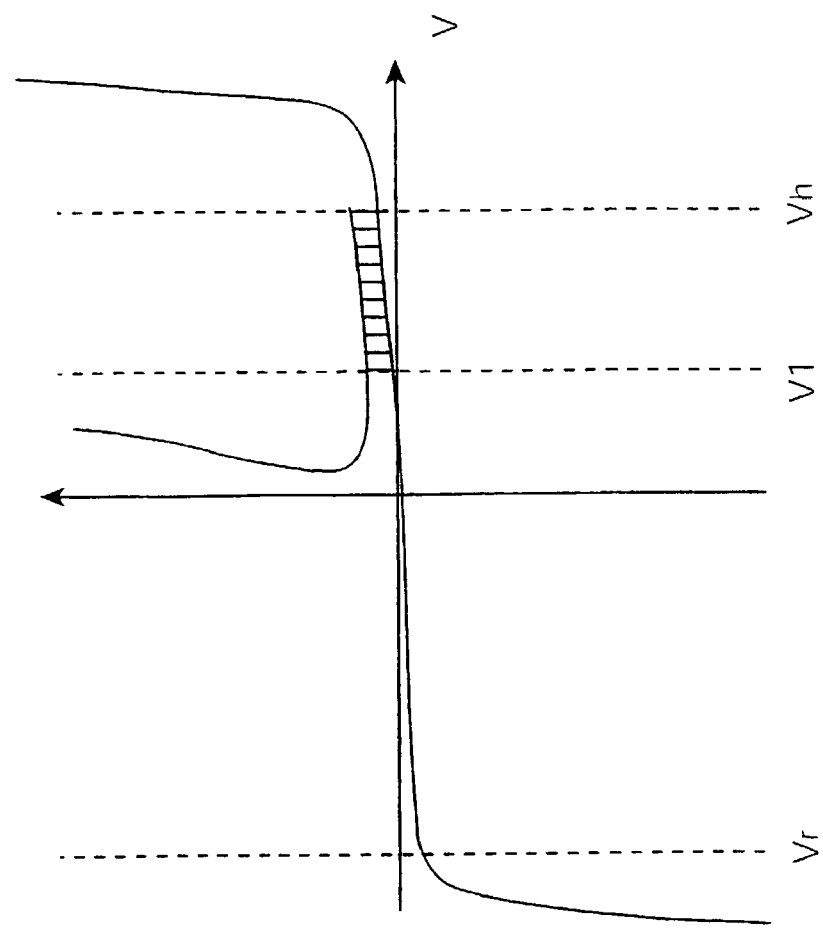
Figure 4B:
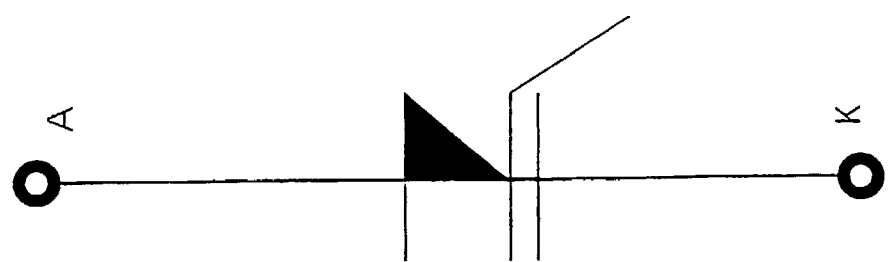

FIG. 4a shows another USD where the device has been configured to change to a state of low impedance if the instantaneous voltage across the anode A' and cathode K' exceeds a well defined threshold Vl, yet does not exceed an even higher voltage threshold Vh. In other words, if the voltage V applied across the device in FIG. 4a is within a well specified range from Vl to Vh the device will enter its low impedance state, while if it is outside this range, the device will remain in its default high impedance mode. With this particular characteristic the device is termed a "breakunder" USD. FIGS. 4b and 4c show the device's circuit symbol and IV characteristics respectively.

The implementation of the breakunder USD in FIG. 4a is similar to that of the breakover device in FIG. 3. The main difference is the presence of a capacitor C1 and a second transistor T2. Capacitor C1 limits the rate of change of voltage across R1. This in turn limits the rate of change of voltage across the DIAC. Since the voltage across the DIAC is slow to rise, if the voltage Y at the base of T2, as determined by the voltage divider R4/R5, rises above the forward bias voltage across T2's base emitter-junction before the DIAC voltage reaches its threshold Vd, the transistor T2 will turn on to short the gate of the TRIAC to K' and thus inhibit any current flow into the gate of the TRIAC. Using this arrangement, the upper voltage threshold Vh can be set by the voltage divider R4/R5 and the lower threshold Vl can be set as before by R1/R2.

Any breakunder device can further be arranged so that, once a voltage has been applied across its terminals large enough to exceed the upper threshold Vh so keeping the device in the high impedance state, if the applied voltage drops in magnitude the device will remain in the high impedance state. In this mode, in order to change to the low impedance state, the current must be reduced to almost zero and then re-applied. This later device is referred to as a breakunder USD with hysteresis.

Figure 5A:
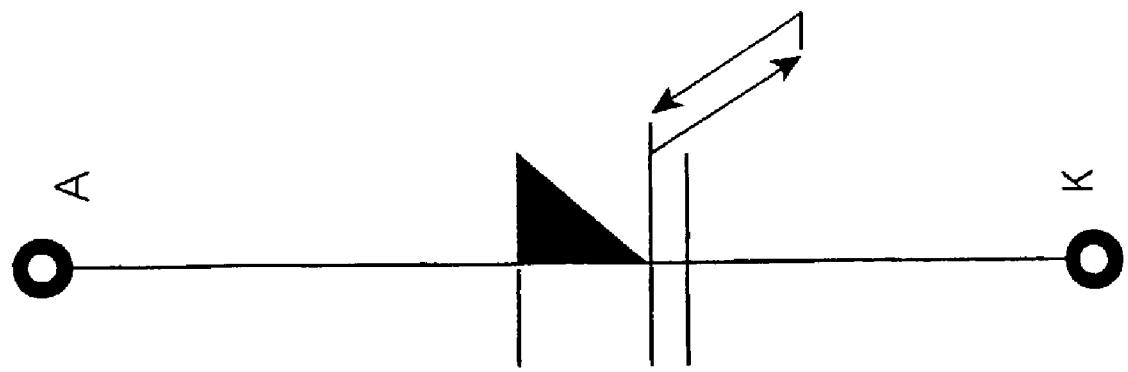
FIGS. 5a and 5b are, respectively, the circuit symbol and a circuit diagram for a breakunder USD with hysteresis.
Figure 5B:
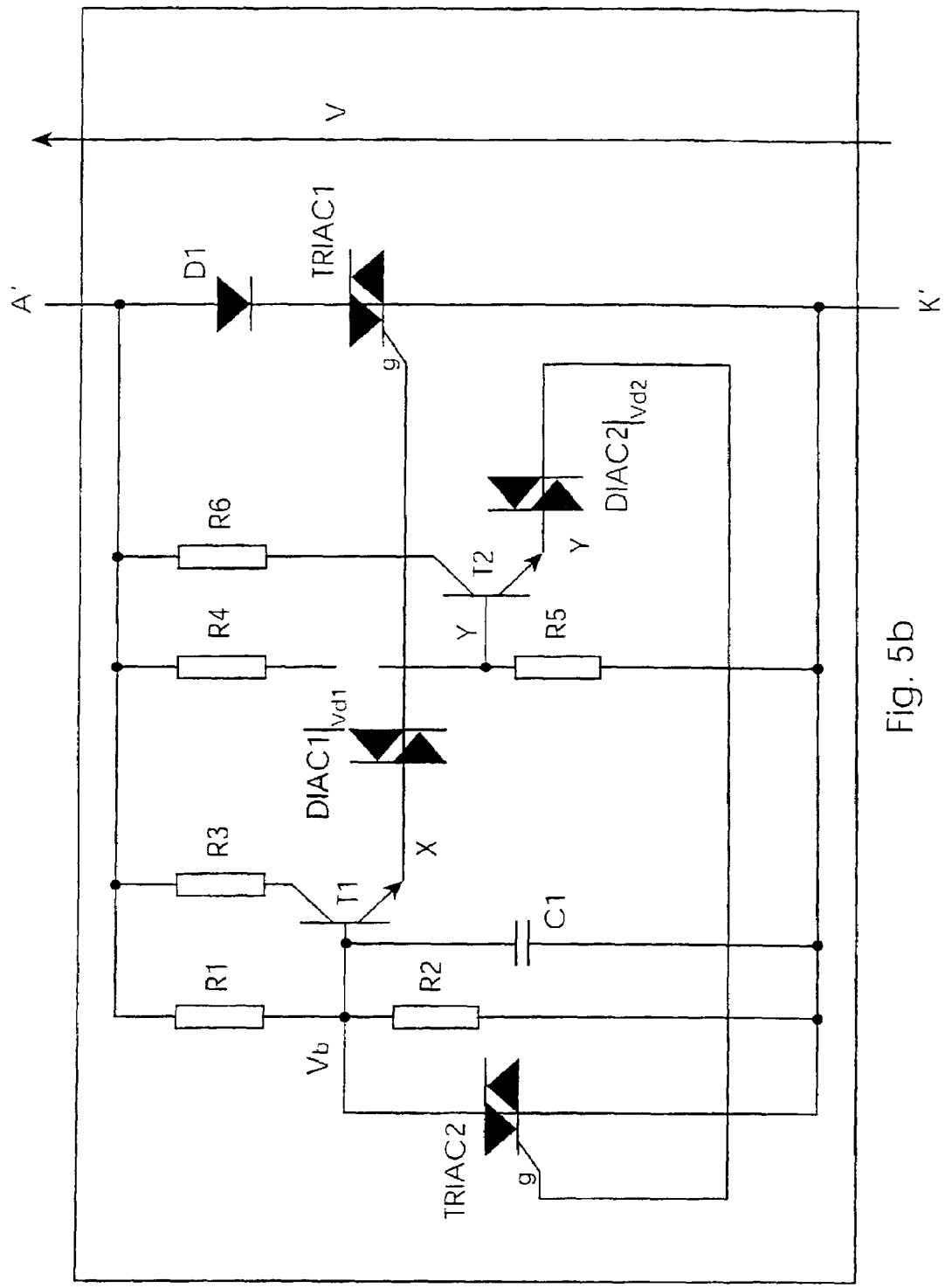

FIG. 5a shows the circuit symbol for a breakunder USD with hysteresis. FIG. 5b shows an implementation of the device based upon the breakunder device shown in FIG. 4. Only the differences will be described. A transistor T2 now forms a second emitter follower supplying a second DIAC, DIAC2. The voltage at point Y is designed to have a value equal to the threshold of DIAC2 when the voltage V across A', K' is equal to an upper threshold Vh. From FIG. 5b it can be seen that, unlike the voltage at point X, the voltage at point Y will instantaneously follow V and will be a proportion of V according to the ratio set by R4 and R5. If the voltage V causes the voltage at Y to exceed the voltage threshold of DIAC2, then a second TRIAC, TRIAC2, will enter a low impedance state. As soon as TRIAC2 enters its low impedance stare, the voltage Vb at the base of T1 will reduce to almost zero. Once TRIAC2 has entered a low impedance state T1 cannot supply any current to DIAC1 and therefore the gate of TRIAC1. This "feedback" enhancement of FIG. 4 has introduced a level of hysteresis in to the arrangement. The only way now for TRIAC1 to enter its low impedance state is for the voltage across A', K' to be reduced to zero and then a new voltage applied which has a value between the lower threshold set by R1, R2 and DIAC1 and the upper threshold set by R4, R5 and DIAC2. This device has essentially three modes, two high impedance and one low impedance. If the instantaneous voltage applied to the arrangement is below the lower threshold Vl, then the combination of R1, R2 and T1 means that DIAC1 does not pass current and TRIAC1 remains in it's high impedance state. If the applied voltage is greater than the Lower threshold Vl and less than the upper threshold Vh, then the combination of R4, R5 and T2 means that DIAC2 does not pass current and with DIAC1 now passing current, once the voltage across C1 has had sufficient time to rise, to the gate of TRIAC1, TRIAC1 enters its low impedance state. If, however, the applied voltage is greater than the upper threshold Vh, then the combination of R4, R5 and T2 means that DIAC2 does pass current to the gate of TRIAC2 thereby inhibiting DIAC1 and keeping TRIAC1 in its high impedance state.

It should be noted that any of the USDs of FIGS. 3 to 5 could be implemented as doped silicon layers in a single discrete integrated device. None of the devices require any external control and have the characteristic that they will conduct if the voltage across their two terminals A' and K' is either above and/or below a specified threshold. Another characteristic is that once in their low impedance state, they can only be returned to their high impedance state if the current flow through them is reduced to near zero. At exactly which current they will drop-out is dependent upon the particular device used.

Figure 6:
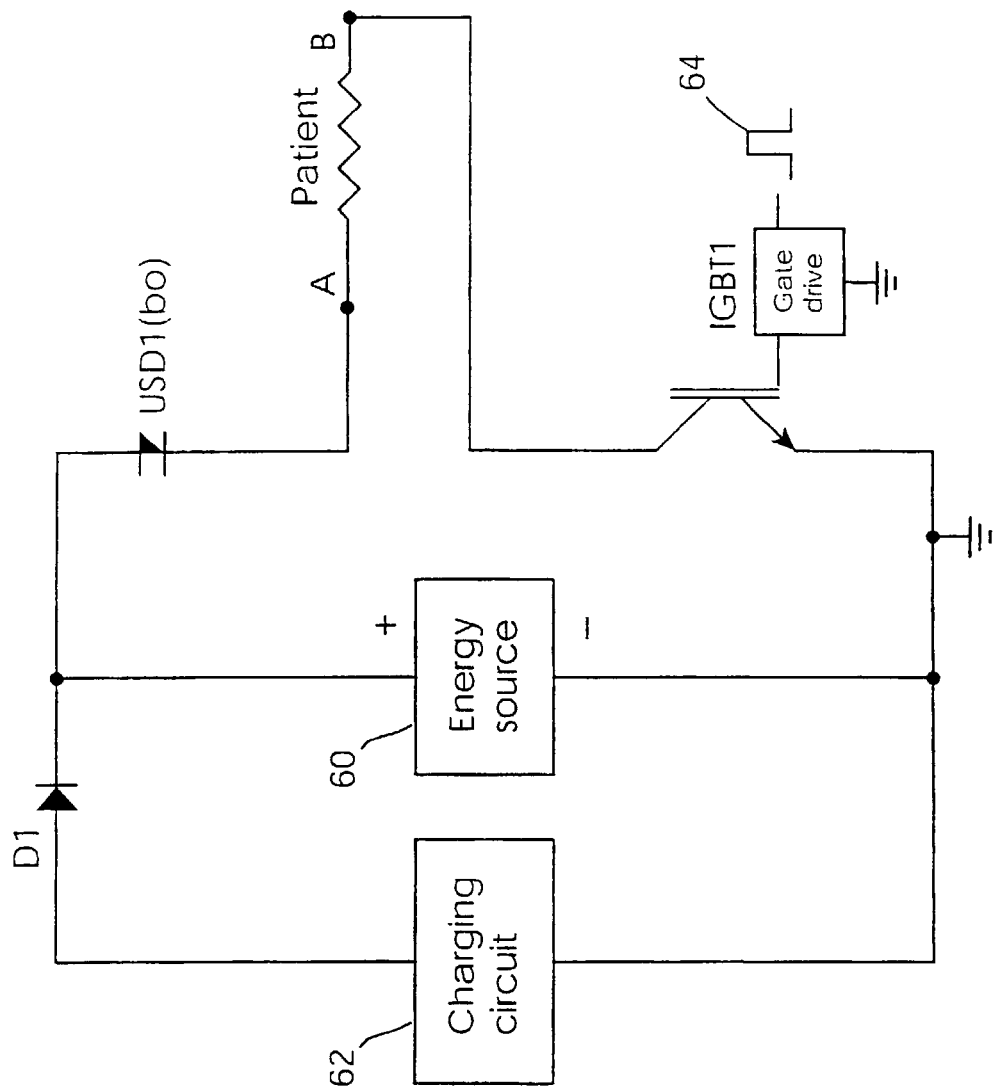
FIG. 6 is a circuit diagram of a first embodiment of defibrillator according to the invention.

FIG. 6 shows a basic embodiment of a defibrillator according to the invention, designed to provide a monophasic output voltage pulse across a pair of patient electrodes A and B. The defibrillator has an energy source 60, in this instance a capacitor which is charged up by a charging circuit 62, and an output circuit for connecting the voltage on the capacitor across the electrodes A, B upon the occurrence of a control signal 64. The output circuit comprises a first current path connecting the +ve side of the energy source 60 to the electrode A and a second current path connecting the −ve side of the energy source to the electrode B. The first current path contains a breakover USD, USD1 (bo), while the second current path contains an IGBT, IGBT1. The breakover USD1(bo) will allow the current from the energy source 60 to flow through the load (patient) connected across the output electrodes A and B if the voltage applied from the energy source is large enough to exceed its threshold. The breakover USD1(bo) can be constructed as described with reference to FIG. 3.

Initially, both sides of the load see a high impedance into A and B. Applying a gate drive pulse 64 to IGBT1 turns the latter on and drops the entire energy source voltage across USD1(bo). Provided the energy source is charged to a voltage above the threshold for USD1(bo), the latter will change to its low impedance state. The energy source now begins to discharge into the load. Removing the drive pulse 64 from the gate of IGBT1 after a pre-determined time period causes IGBT1 to return to its high impedance state and the current in the circuit reduces to approximately zero. With almost zero current flow, the device USD1(bo) recovers and the load once again sees a high impedance on both sides of A and B.

The use of the USD between electrode A and the +ve terminal of the energy source means that there is no isolated controlling circuit connection required. The only controlling element in the circuit of FIG. 6 is the gate of IGBT1 and this is referenced to the circuit ground so no isolation barrier is needed. The conventional diode D1 is used to prevent current flow back into the charging circuitry when charging is complete. The output generated by the circuit of FIG. 6 is a simple monophasic truncated exponential waveform.

Although FIG. 6 shows only one USD in the first current path, it will be understood that the voltage that can be withstood by the output circuit in the high impedance state can be increased by totem-poling two or more USDs in the first current path, as described previously. Two or more USDs in series actually behave just like a single USD with a threshold Vth which is the sum of the thresholds of the individual devices.

Figure 7:
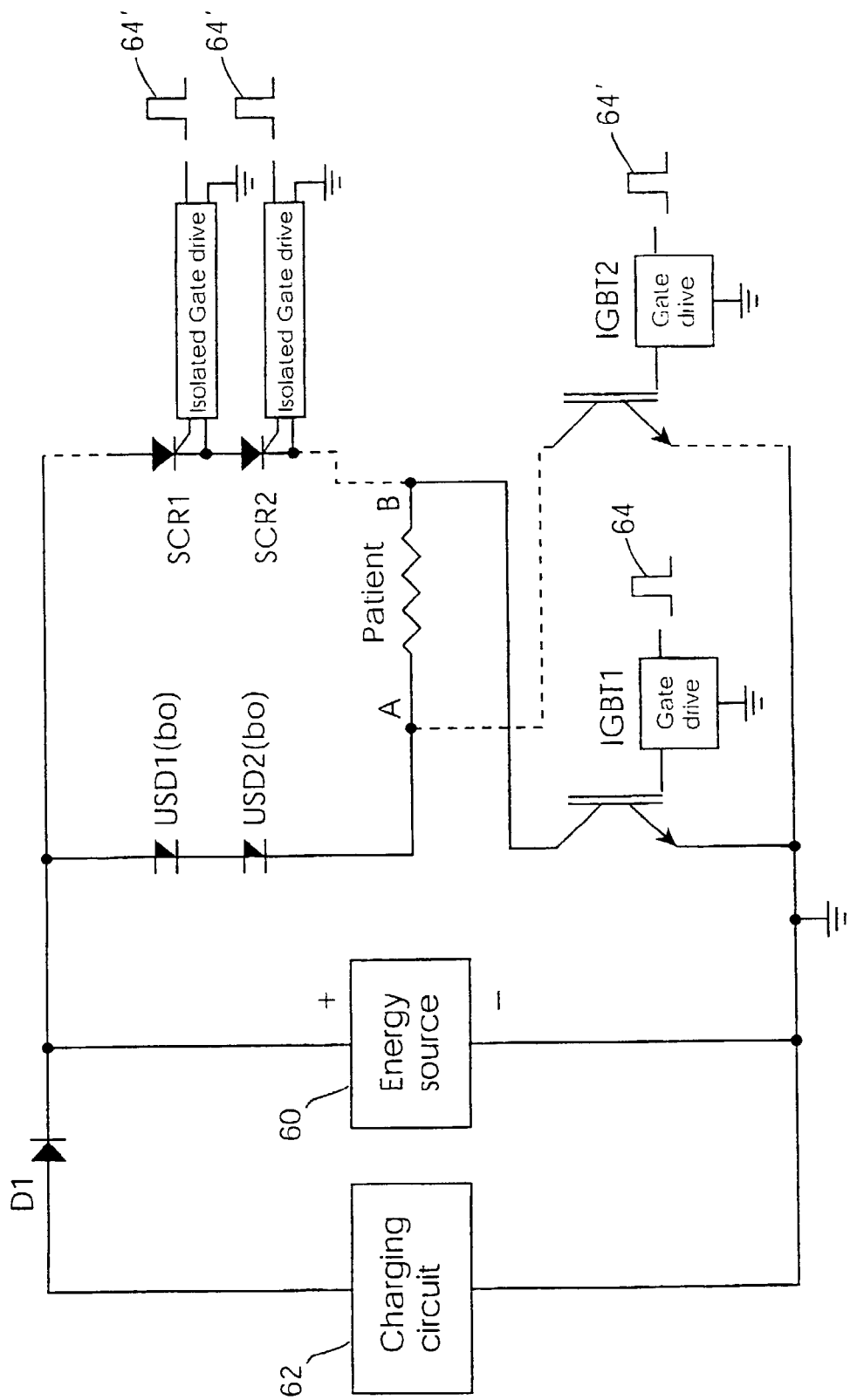
FIG. 7 is a circuit diagram of a second embodiment of defibrillator according to the invention.

FIG. 7 shows an embodiment of a defibrillator according to the invention, designed to provide a biphasic truncated exponential output voltage pulse across the patient electrodes A and B. Essentially, the embodiment of FIG. 6 has been modified to add third and fourth current paths, shown by dashed lines. The third current path connects the +ve side of the energy source 60 to the electrode B and the fourth current path connects the −ve side of the energy source to the electrode A. The third current path contains two "totem-poled" SCRs, SCR1 and SCR2, while the fourth current path contains a further IGBT, IGBT2. The first and second current paths are as before, except that the first current path is shown with two totem-poled breakover USDs, USD1(bo) and USD2(bo). The USDs may be as shown in FIG. 3. For reasons previously described, the SCRs have isolated gate drives.

In operation, the energy source 60 is first charged to a voltage exceeding the threshold Vth of the totem-poled USDs. Then, at time t0 (see FIG. 8), the device IGBT1 is given a gate pulse 64 placing it into its low impedance state. This places substantially the entire voltage of the energy source across the totem-poled USDs (two USDs are used as previously stated to increase the voltage that the circuit can withstand). The USDs therefore turn on (the devices SCR1, SCR2 and IGBT2 remaining in their high impedance state), and a current flows through the load from electrode A to electrode B. As energy is removed from the energy source by the load, the voltage applied by the energy source decays. At a later time t1, the IGBT1 has its gate signal removed and it returns to its high impedance state. This causes the current in the circuit to reduce to almost zero so returning the devices USD1(bo) and USD2(bo) to their high impedance states. The instant t1 is chosen so that at that point the voltage remaining on the energy source is below the threshold Vth of the totem-poled devices USD1(bo) and USD2 (bo).

Figure 8:
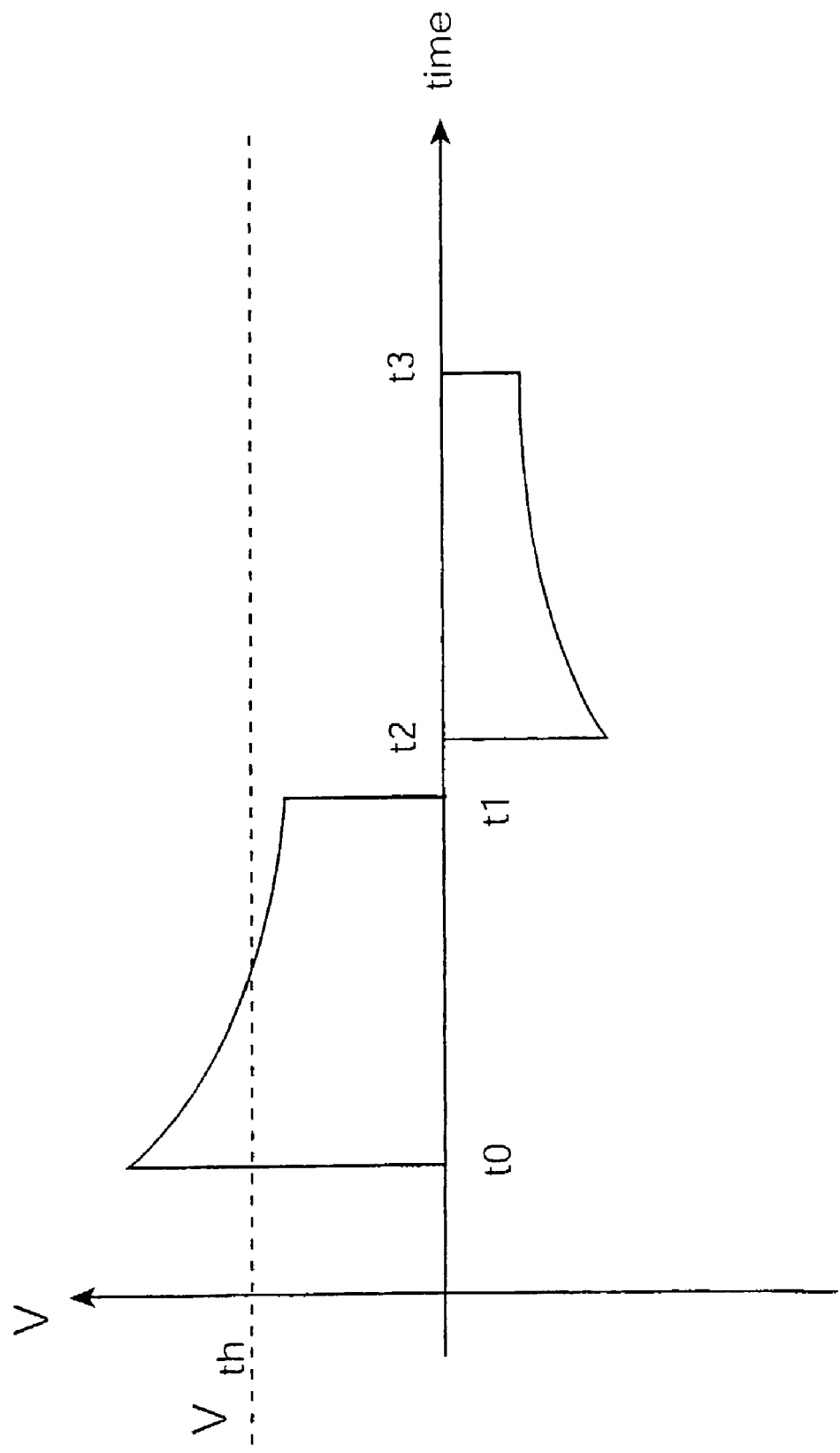
FIG. 8 is an example of the waveform that can be produced by the embodiment of FIG. 7.

Now, at a time t2 following shortly after t1, the devices IGBT2, SCR1 and SCR2 are given simultaneous gate drive pulses 64' to place them in their low impedance state. Now a discharge current flows in the opposite direction through the load, i.e. from electrode B to electrode A. After a further pre-determined time period has elapsed the gate drive to device IGBT2 is removed at t3 and the current flowing in the circuit is reduced almost to zero. Again this causes the two SCRs to also return to their high impedance state. The resulting output is as shown in FIG. 8.

In this circuit isolated gate drives are required for the SCRs. However, only two such isolated gate drives are required in this case. The methods used by prior art would have required at least four isolated gate drive circuits. Also only four devices are required to be controlled in total instead of the six control lines previously necessary.

Figure 9:
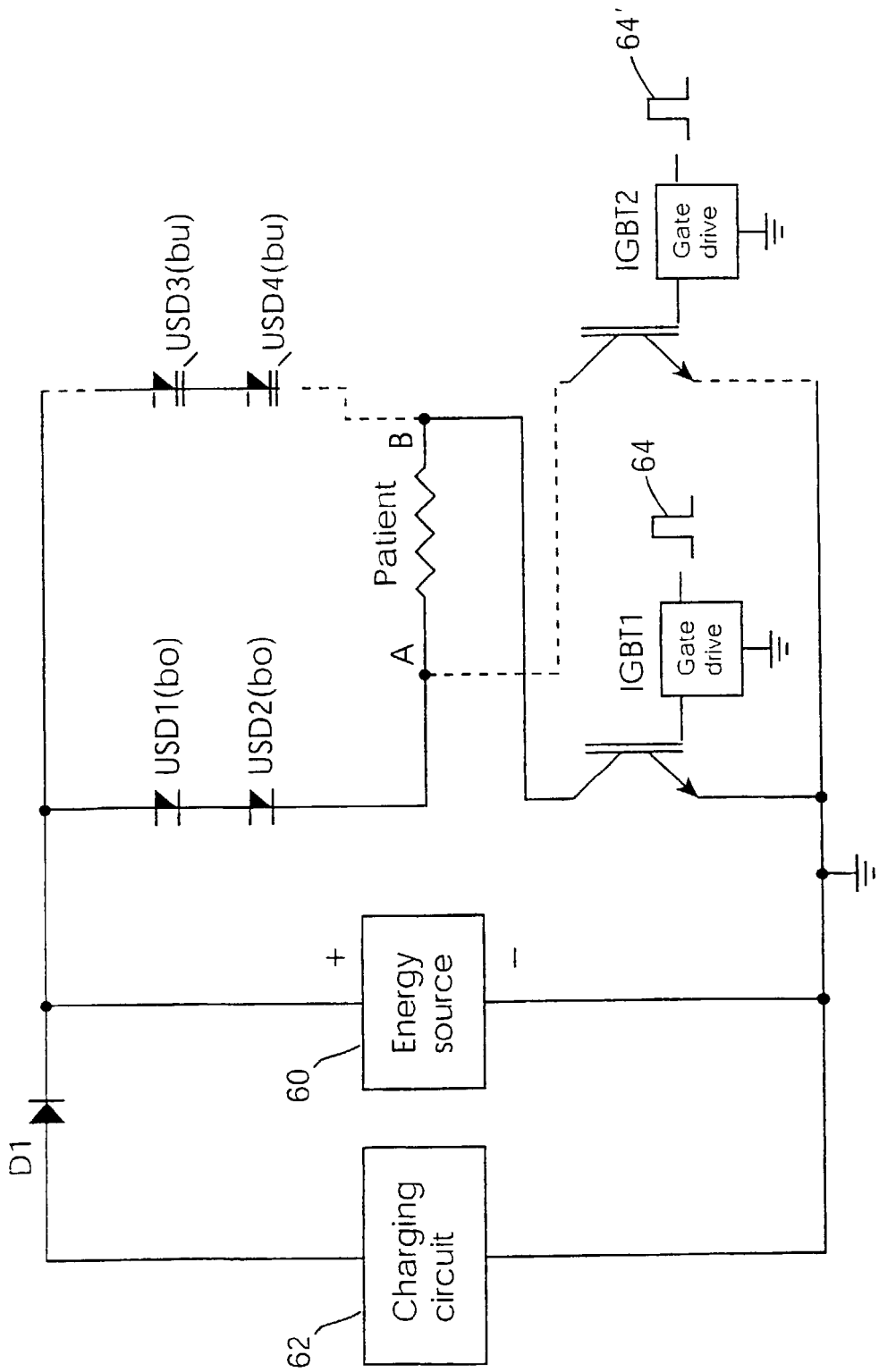
FIG. 9 is a circuit diagram of a third embodiment of defibrillator according to the invention.

FIG. 9 shows a third embodiment of the invention. This differs from the embodiment of FIG. 7 in that the totem-poled SCRs, SCR1 and SCR2, have been replaced by totem-poled breakunder USDs with hysteresis, USD3 (bu) and USD4 (bu).

In operation, the energy source 60 is first charged to a voltage greater than the threshold Vth of the totem-poled breakover USDs and also greater than the upper voltage threshold Vh of the totem-poled breakunder USDs. Then, at time t0 (see FIG. 8, which also apples in this case), the device IGB1 is given a gate pulse 64 placing it into its low impedance state. This places substantially the entire voltage of the energy source across the totem-poled breakover USDs, USD1(bo) and USD2(bo). All other devices remain in their high impedance state (the breakunder USDs because the voltage is above their upper threshold Vh; this is important because otherwise they would turn on and bypass the load). The breakover USDs therefore turn on and a current flows through the load from electrode A to electrode B. As energy is removed from the energy source by the load, the voltage applied by the energy source decays. At a later time t1, the IGBT1 has its gate signal removed and it returns to its high impedance state. This causes the current in the circuit to reduce to almost zero so returning the devices USD1(bo) and USD2(bo) to their high impedance states. The instant t1 is chosen so that at that point the voltage remaining on the energy source is below the threshold Vth of the totem-poled devices USD1(bo) and USD2(bo) but between the upper and lower voltage thresholds Vl, Vh of the totem-poled devices USD3 (bu) and USD4 (bu).

Now, at a time t2 following shortly after t1, the device IGBT2 is given a gate drive pulse 64' to place it in its low impedance state. Now the devices USD3 (bu) and USD4 (bu) turn on, because the voltage applied across them is between their upper and lower voltage thresholds, and a discharge current flows in the opposite direction through the load, i.e. from electrode B to electrode A. After a further pre-determined time period has elapsed the gate drive to device IGBT2 is removed at t3 and the current flowing in the circuit is reduced almost to zero. Again this causes USD3 (bu) and USD4 (bu) to return to their high impedance state. The resulting output is as shown in FIG. 8.

Of particular note is that for this arrangement there are no isolated connection gate control connections to any of the devices in the circuit. Also only two devices (IGBT1 and IGET2) require control signals and these are both direct electrical connections referenced to circuit ground. This is a significant saving in size and component cost. Furthermore, to control the entire circuit only requires two control signals rather than the five that would be otherwise be necessary. The control circuit can now simply pulse one IGBT, IGBT1, to produce the first phase of the output waveform and pulse the second IGBT, IGBT2, to produce the second phase of the output.

Figure 10:
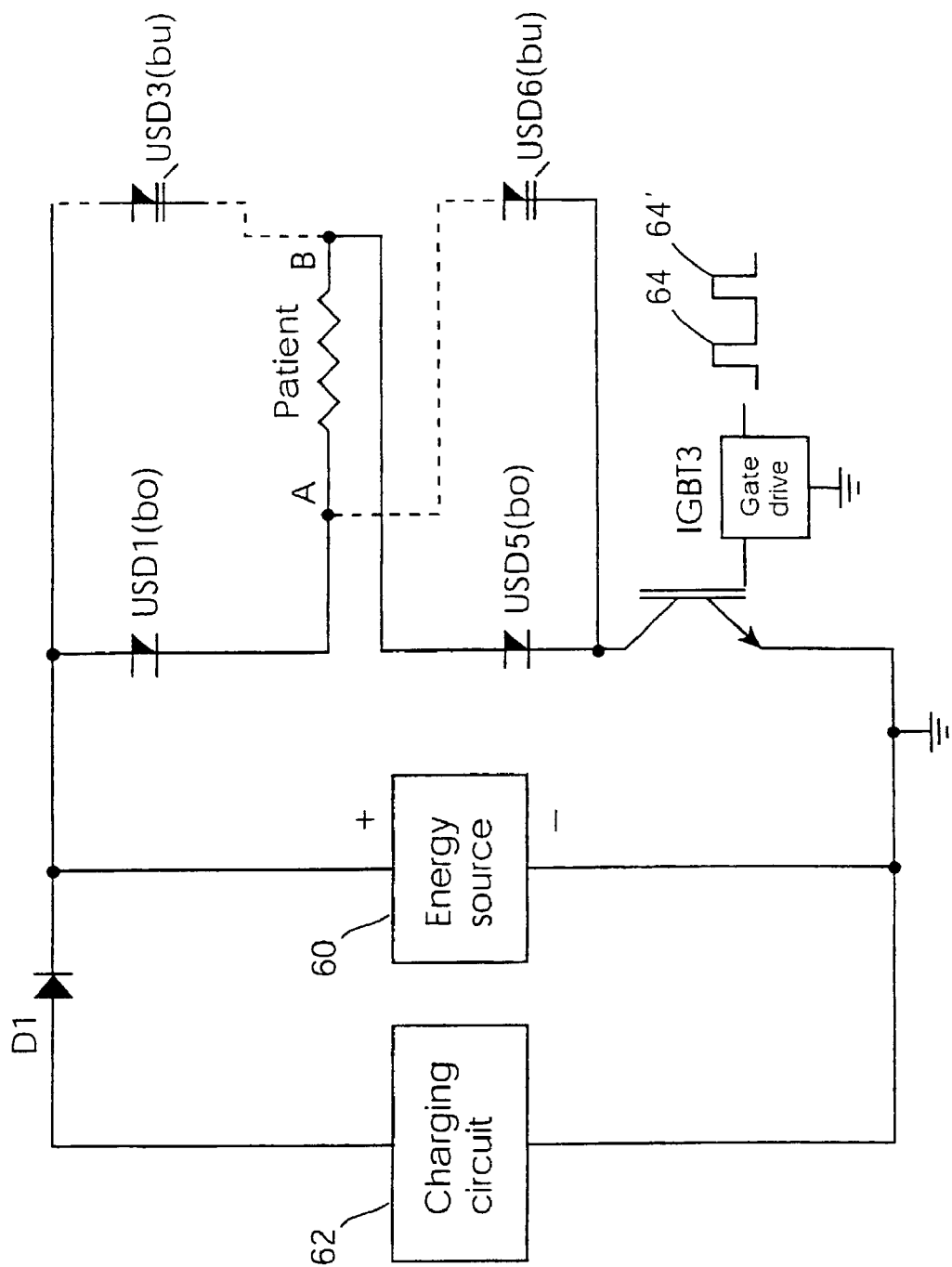
FIG. 10 is a circuit diagram of a fourth embodiment of defibrillator according to the invention.

FIG. 10 shows a fourth embodiment of the invention. This differs from the embodiment of FIG. 9 in that the two IGBTs, IGBT1 and IGBT2, have been replaced by a breakover USD, USD5(bo), and a breakunder USD, USD6(bu), respectively. Also, an IGBT (IGBT3) has been added in common to the second and fourth current paths. For simplicity the circuit uses single USDs (USD1(bo) and USD3(bu) respectively) in the first and third current paths, although as described two or more such devices can be totem-poled in each path to increase the ability of the circuit to withstand higher voltages. Although this arrangement has added another circuit element, IGBT3, the output circuit is fully automatic and all devices connected to the load across A and B are uncontrolled. The only controlling signal required is the signal to the gate of IGBT3 in the common ground return.

In operation, having charged the energy storage device 60 to a voltage greater in magnitude than the threshold of breakover devices USD1(bo) and USD5(bo), and also high enough not to enter the threshold range which would place USD3(bu) and USD6(bu) into their low impedance state, a gate drive pulse 64 applied to IGBT3 will turn on USD1(bo) and USD5(bo) and cause current to follow through the load in the direction from A to B. Removing the gate drive to IGBT3 after a predetermined time interval will, as before, reduce the current in the circuit to almost zero and all devices will return to their high impedance states Provided the voltage across the energy storage device is now less than the threshold for USD1(bo) and USD5(bo), and furthermore providing the voltage is within the threshold required to allow the break-under devices USD3(bu) and USD6(bu) to enter their low impedance states, the application of a second gate pulse 64' to IGBT3 will cause the current to flow through the load in the opposite direction from B to A. Again, this causes the biphasic waveform of FIG. 8 to be generated.

Figure 11:
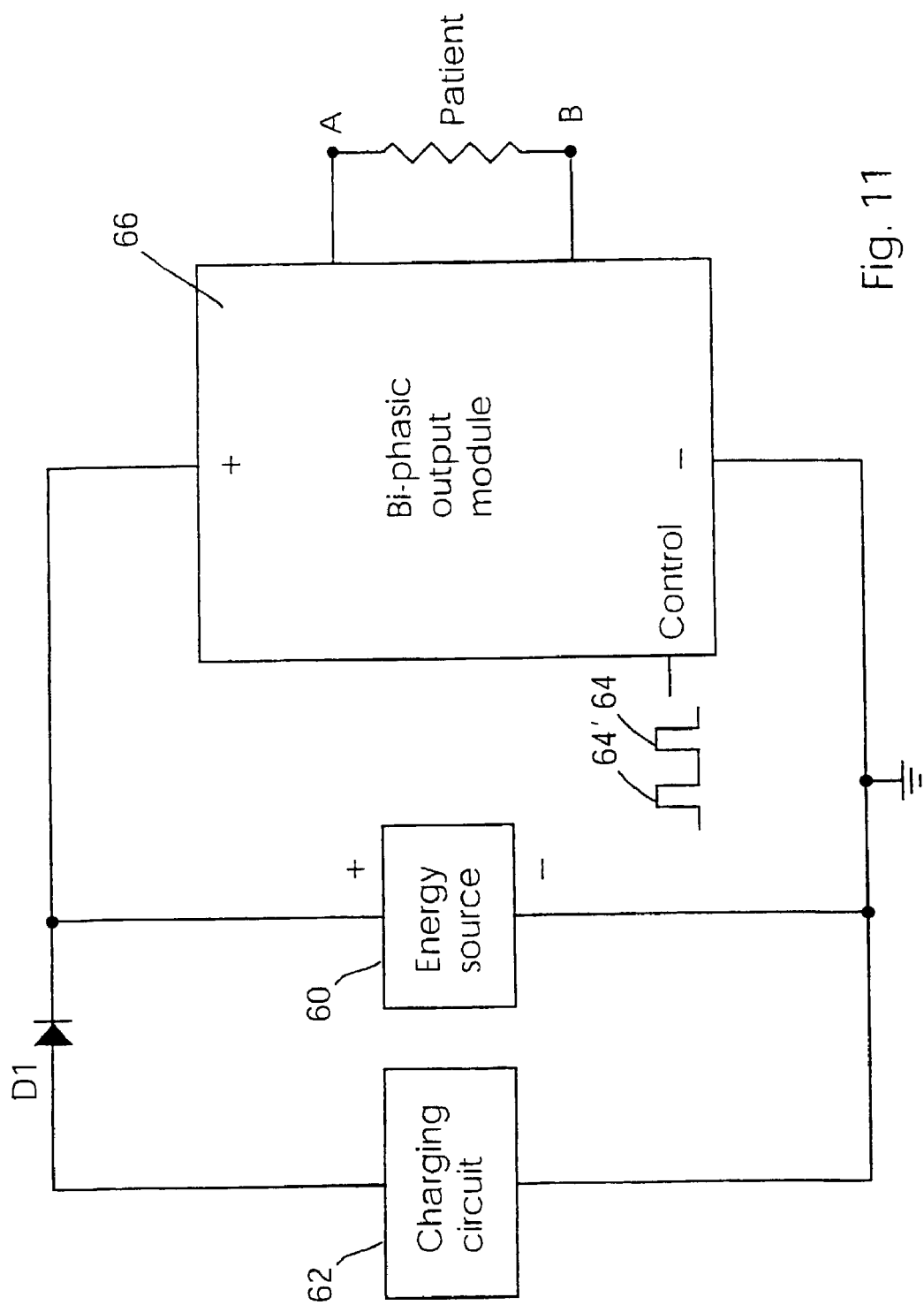
FIG. 11 illustrates the fourth embodiment where the output circuit is implemented as a single encapsulated integrated circuit component.

Note that not only is there no requirement for any isolated connections to any of the devices but only one single device needs to have a gate drive signal applied in order for the whole circuit to be fully operated. It will be appreciated that this arrangement means that the whole output circuit including USD1(bo), USD5(bo), USD3(bu), USD6(bu) and IGBT3 could be easily implemented as a single integrated solid state component. This would further mean that the entire output stage would be a single encapsulated integrated module only requiring 5 connections. These connections would be a common ground connection, an input from an energy source, two output connections to the electrodes A and B and a single input control connection referenced to the common ground which would control the module. FIG. 11 shows the block diagram of a circuit including such an integrated circuit 66—note that even the gate drive circuit for the IGBT can be included in the module, leaving the control terminal into the circuit requiring a standard TTL type signal. This represents an enormous saving in terms of cost, size and complexity.

Figure 12A:
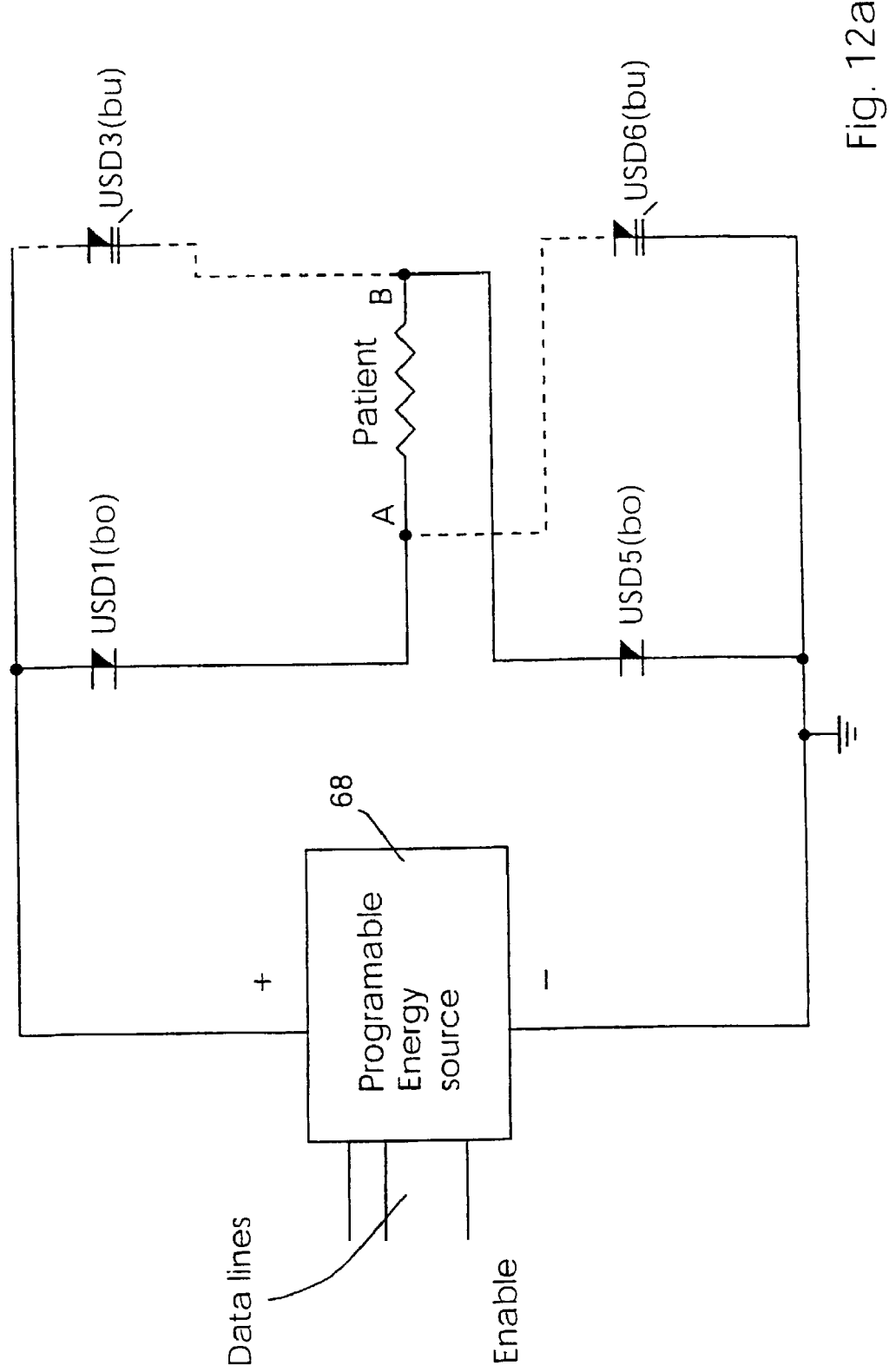
FIG. 12a is a circuit diagram of a fifth embodiment of defibrillator according to the invention.
Figure 12B:
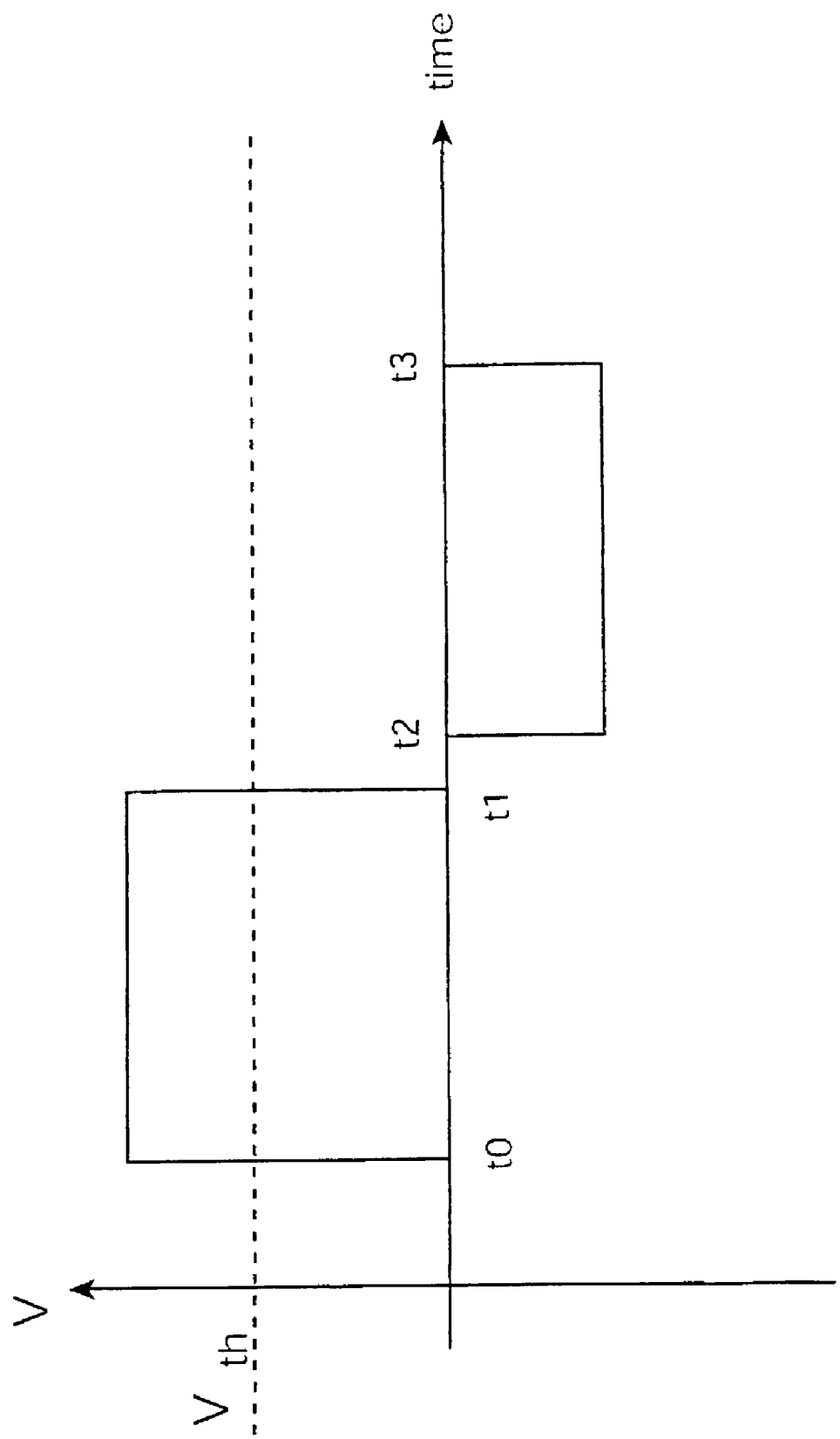

In a fifth embodiment of the invention, which is a modification of that shown in FIG. 10, and may likewise be formed with the output circuit as a single integrated circuit component, the energy source is a programmable active power supply 68, rather than a passive capacitor. Referring to FIG. 12a, here the energy source is designed to supply a programmed constant DC voltage, and with this voltage set at a level above the conducting threshold Vth of breakover devices USD1(bo) and USD5(bo) and greater than the low impedance threshold range of break-under devices USD3 (bu) and USD6(bu), the current again flows through the load from A to B. Setting the programmable power supply then to supply a voltage of zero volts for a pre-determined time interval causes all the devices to return to their high impedance state. Further setting it to supply a voltage which is less than the thresholds for USD1(bo) and USD5(bo), and within the threshold range required to allow the breakunder devices USD3(bu) and USD6(bu) to enter their low impedance state, will cause the current to flow in the opposite direction from B to A. The resulting waveform can be seen by way of example in FIG. 12b. It would also be possible to have several energy sources selectable by placing additional USDs within the circuit arrangement. Which energy source is to be used to supply the output circuit could then be selected at whatever times are desirable to achieve the pulse shape required.

The invention therefore provides an improved means to generate a large variety of pulses and pulse shapes, but does so with less components and a much greater simplicity than is currently available by other means.

It should be appreciated that further current paths containing USDs or other solid state devices could be added between the energy source and the electrodes A and B in any of the circuits described above, thereby allowing a third, fourth or subsequent phase to be added in a pre-determined polarity.

It should also be appreciated that further protective components may be necessary for reliable operation of the circuits in practice. By way of example, an inductor could be placed in series with the output of the energy source to limit the rate of change of current in the circuit. Such additions are well known to those skilled in the art.

As previously shown, the use of totem-poling to increase the amount of voltage that the circuit can withstand is well known to those skilled in the art. In all the preceding embodiments, therefore, each current path to or from an electrode A or B can contain only a single USD or other solid state device or two or more such devices totem-poled according to voltage requirements.

The invention is not limited to the embodiments described herein which may be modified or varied without departing from the scope of the invention.

The invention claimed is:

1. A defibrillator comprising first and second electrodes for application to a patient, a voltage source, and an output circuit for connecting the voltage source across the electrodes upon the occurrence of at least one control signal, wherein the output circuit includes a first current path connecting one side of the voltage source to the first electrode and a second current path connecting the other side of the voltage source to the second electrode, a third current path connecting the one side of the voltage source to the second electrode, and a fourth current path connecting the other side of the voltage source to the first electrode, each of the first to fourth current paths containing at least one solid state switching device that is an uncontrolled two-terminal device which automatically undergoes a transition from a high impedance state to a low impedance state when a voltage greater than a predetermined threshold is applied across its terminals, the at least one switching device in the first current oath transitioning to a low impedance state unconditionally when the applied voltage exceeds a predetermined threshold, and the at least one switching device in the third current oath transitioning to a low impedance state if the applied voltage exceeds a predetermined first threshold but not a second, higher threshold.

2. A defibrillator as claimed in claim 1, wherein each of the second and fourth current paths contains a controlled solid state switching device.

3. A defibrillator as claimed in claim 1, wherein the the at least one switching device in the second current path transitions to a low impedance state unconditionally when the applied voltage exceeds a predetermined threshold and the at least one switching device in the fourth circuit path transitions to a low impedance state if the applied voltage exceeds a predetermined first threshold but not a second, higher threshold, the output circuit also including a controlled solid state switching device common to the second and fourth current paths.

4. A defibrillator as claimed in claim 1, wherein the voltage source is a capacitor.

5. A defibrillator as claimed in claim 1, wherein the voltage source is a programmable voltage source.

6. A defibrillator as claimed in claim 1, wherein the output circuit is a single integrated solid state device.

* * * * *